United States Patent [19]
Lussow et al.

[11] Patent Number: 5,922,548
[45] Date of Patent: Jul. 13, 1999

[54] ANTI α-GAL SCREENING TECHNIQUE

[75] Inventors: Alexander R. Lussow, Menlo Park; Roland Buelow, Palo Alto; Philippe Pouletty, Atherton, all of Calif.

[73] Assignee: SangStat Medical Corporation, Manlo Park, Calif.

[21] Appl. No.: 08/942,807

[22] Filed: Oct. 2, 1997

Related U.S. Application Data

[62] Division of application No. 08/740,166, Oct. 22, 1996., Pat. No. 5,714,332
[60] Provisional application No. 60/006,044, Oct. 24, 1995.
[51] Int. Cl.$^6$ .................. G01N 33/53; G01N 33/554; C07K 4/00
[52] U.S. Cl. ............. 435/7.1; 436/519; 435/7.2; 435/7.21; 530/300; 536/23.1
[58] Field of Search .................. 436/519; 435/7.1, 435/7.2, 7.21; 530/300; 536/23.1

[56] References Cited

FOREIGN PATENT DOCUMENTS

94/02515  7/1993  WIPO .
95/24924  3/1995  WIPO .

OTHER PUBLICATIONS

Guerif, F., et al., "Screening of Pig cDNA Expression Library with Human Serum in Order to Identify New Xenoantigens," *Cambridge Sci. Abs.*, Acc. Nr.: 01971387 3820007, 1995., *Transplantation proceedings*, 27(4):2941 (1995).

Galili, U., et al., "Evolutionary Relationship Between the Natural Anti–Gal Antibody and the Galα1→3Gal Epitope in Primates," *PNAS, USA*, 84:1369–1373 (1987).

Galili, U., et al., "One Percent of Human Circulating B Lymphocytes are Capable of Producing the Natural Anti–Gal Antibody," *Blood*, 82(8):2485–2493 (1993).

Galili, U., et al., "Human Natural Anti–α–Galactosyl IgG. II. The Specific Recognition of α(1→3)–Linked Galactose Residues," *J. Exp. Med.*, 162:573–582 (1985).

Nakagawa et al (FEBS Letters, 408:301–305, 1997.

Ennas et al (Cancer Research, 57:2035–2041), 1997.

*Primary Examiner*—Paula K. Hutzell
*Assistant Examiner*—Susan Ungar
*Attorney, Agent, or Firm*—Richard F. Trecartin; Flehr Hohbach Test Albritton & Herbert LLP

[57] ABSTRACT

Compounds and libraries are labeled with a galactosyl epitope and then screened in accordance with an assay involving cells having a characteristic of interest. Conveniently, the screening may embody target cells, where the compounds are brought in contact with the cells. Each of the compounds carries with it the information of its identity or method of synthesis. After washing away non-specifically bound compounds, blood may be applied to the cells, whereby antibody binding to the galactosyl epitope initiates the complement cascade. Plaques are identified and the compound associated with the plaque identified. The formation of the plaque demonstrates that the compound has specific affinity for the target cell, binding of the compound to the cell does not interfere with binding of the antibody, and that the complex is capable of cytotoxic activity by means of the complement cascade.

9 Claims, No Drawings

ANTI α-GAL SCREENING TECHNIQUE

This application is a divisional of U.S. Ser. No. 08/740,166, filed Oct. 22, 1996, now U.S. Pat. No. 5,714,332, issued Feb. 3, 1998, which claims the benefit of provisional application Ser. No. 60/006,044, filed Oct. 24, 1995, now abandoned.

TECHNICAL FIELD

The field of this invention is the screening of compounds for binding to a molecular target.

BACKGROUND

The drug industry has continuously depended upon the discovery of new compounds, which can be used to treat a continuously increasing number of diseases. As the ability to detect various pathogenic agents increases, one has the opportunity to develop new therapeutic agents which have specificity for one or more pathogens. In addition, there are numerous cellular markers (including receptors) associated with individual cells, as related to tissues, mobile cells, organs, levels of differentiation, and the like. In many instances, binding to these markers will transduce signals across the membrane, so as to initiate or inhibit intracellular processes. These processes may involve activation/inactivation, differentiation, secretion, proliferation, cytotoxic activity, metabolism of various nutrients, and the like. In many situations, one wishes to have compounds which act as agonists or antagonists to these various processes. In addition, one may wish to selectively kill various cells or deactivate various cells. For example, with cancers it would be very desirable to be able to selectively kill the cancer cells, while not affecting normal cells.

Furthermore, many of the drugs which are used today have a plurality of effects. Rather than exerting the particular effect of interest, the drugs bring with them a train of other effects, which may be deleterious to the host. In most cases, the deleterious effects are because the drug is not as specific for the target as one would wish, so as to bind other targets and induce the undesirable side effects.

The synthesizing of new compounds or identifying new compounds in nature is extraordinarily expensive. Therefore, for the most part, the repertoire of potential pharmacophores is relatively limited. Rational drug design has provided some insights, but has not been as successful as one hoped. The situation is particularly complicated because it has been found that as a drug binds to its' receptor, the conformation of the receptor may change. Therefore, the spatial conformation of the binding site may undergo substantial changes depending upon the manner in which the receptor and drug interact, and this has important implications when designing drugs.

In order to add greater variety to compounds available for drug development, combinatorial libraries have been created. These libraries are predicated on being able to prepare large numbers of compounds, particularly thousands of compounds, within a relatively short time; combinatorial libraries can be randomly created without a motif, where the diversity can be $10^{12}$ compounds. Initially, the compounds were for the most part oligomers, where the same bifunctionality was employed, having different side groups, by being added successively to form the oligomer. This approach lent itself very well to oligopeptides and oligonucleotides. Indeed, the oligopeptides have been expanded to using a wide variety of amino acid analogs, rather than the naturally occurring amino acids. In this way, chains having very different side groups and different intervening moieties between the carboxyl group and the amino group have been prepared. More recently, combinatorial libraries have been shown to be capable of incorporating synthetic organic molecules based on a central pharmacophore.

With combinatorial libraries, the diversity of compounds is no longer the limiting factor in drug development. Instead, screening for compound activity has become the limiting step. In order to be able to screen large numbers of compounds rapidly for a particular characteristic, one needs to have relatively inexpensive, rapid techniques, which have a high degree of fidelity. In addition, the technique should afford the ability to identify the compound which has the desired therapeutic characteristic. Thus, any assay technique should allow for procedures where activity can be readily detected and the identity of the compound having the activity identified.

Relevant Literature

See Galili et al., *J. Exp. Med.* (1985) 162:573–5;82; Galili et al, *PNAS* (1987) 84:1369–1373; and Galili et al., *Blood* (1993) 82:2485–2493. See also, references concerned with combinatorial libraries, supra. See McClellan, *Oral* 34[250] of the Third International Congress for xenotransplantation abstracts, Sep. 27–Oct. 1, 1995 for a peptide mimeotope of Gal α-1,3-galactose.

SUMMARY OF THE INVENTION

Methods and compositions are provided for rapidly screening large numbers of compounds for binding activity as well as directly providing compounds having specific cytotoxic activity. The method provides for bonding hapten such as an α-galactosyl moiety to the compounds in a combinatorial library. The modified compounds may then be contacted with cells or target molecules, where the effect of the contact is individually distinguishable, e.g. spread on a lawn of target cells or incubated with target molecules where each compound at each site can be identified. The cells or molecules are then washed to remove non-specifically bound compounds. An antibody dependent cytotoxic system is then added to the cells, where antihapten (such as anti-α galactosyl) antibodies bind to the compounds bound to the cells and initiate lysis. Lysis of the cells indicates that the compound specifically bound to the cell. By comparing two analogous cells, for example, by having two cellular lawns, differing in known surface receptors and comparing the results of contact with them members of the library, e.g. sites of plaques, one can identify those compounds binding to the receptors present in one lawn and absent in the other lawn. In addition, the galactosyl modified compounds which specifically bind to a target can be used as cytotoxic drugs regardless of their effect on the target receptor as agonists or antagonists.

DESCRIPTION OF THE SPECIFIC EMBODIMENTS

In accordance with the subject invention, methods are provided for identifying compounds having specific affinities for target surface membrane compounds. Particularly, by employing libraries of compounds, where the galactosyl epitope (in reference to the "galactosyl epitope" is intended any compound which specifically binds to an antibody specific for α-galactosyl) is universally bound to the various compounds, the library can be screened for specific binding to the target cells. The interaction of each compound with the cells will be individually distinguishable. By combining the compounds of the library with the target cells in the presence of human polyclonal antibodies, immunoglobulin specific for the galactosyl epitope will bind to the cells through the intermediacy of the compound-galactosyl conjugate. The formation of the immune complex by binding of the antibodies in the blood to the galactosyl epitope will initiate the complement cascade. The death of the cell is the result of complement cytotoxicity can be determined and will be indicative of the binding of the compound to the cell. By employing appropriate controls, one can limit the cytotoxicity to compounds binding to a particular surface membrane protein. The resulting compound-galactosyl conjugate may then be used as a cytotoxic agent for killing cells in the presence of the human or primate blood.

The antibody to α-galactosyl is commonly found at high levels in humans. This antibody is reported at levels of 1% of the total IgG percent in human blood. See Galili et al., *J. Exp. Med.* (1985) 162:573–582; Galili et al, *PNAS* (1987) 84:1369–1373; and Galili et al., *Blood* (1993) 82:2485–2, 493. The smallest ligand for the antibody is the epitope Galα1-3Gal referred to as the α-galactosyl epitope. This epitope has been conjugated to beads (Chembiomed, Edmonton, Alberta, Canada), can be readily synthesized and may be conjugated through the first carbon atom of the galactosyl group with a wide variety of conventional functional groups, such as carboxyl, amino, oxy, thio, or the like.

The particular linking group will vary depending upon the compound to which it is conjugated. In some instances, the linking group will be a bond, which can be to the acetyl or the nitrogen group, where the acetyl group may or may not be present. When not a bond, the linking group will generally be of from about 1–20 atoms other than hydrogen, more usually of from about 1–12 atoms other than hydrogen, may be aliphatic, alicyclic, aromatic, heterocyclic, or combinations thereof, saturated or unsaturated, generally having from about 1–12, more usually from about 1–8, particularly from about 1–6 heteroatoms which for the most part will be oxygen, nitrogen, sulfur, and the like.

Where combinatorial libraries are prepared, there can basically be two types: oligomeric, where for the most part, different compounds share the same difunctionality and are added successively to provide the oligomer; and non-oligomeric, where different compounds are combined, usually based on different functionalities, so that the final product is non-oligomeric, usually being a synthetic organic molecule based on a central grouping, with various pendant groups about the central grouping. For the most part libraries will comprise at least 6 compounds, usually at least 10 compounds, more frequently at least 100 compounds, and may comprise 10,000 or more compounds.

For the most part, the oligomeric compounds will have at least 4 members, usually at least about 5 members and normally fewer than 30 members, usually not more than 15 members, more usually not more than 12 members. Their chemistry will usually be based on combinations of carboxyl and amino groups, hydroxyl and phosphate, polyethers, analogs and combinations thereof. Conveniently, for peptide libraries amino acids may be employed which are naturally occurring or synthetic, so that a wide variety of oligomers may be prepared. For the synthetic amino acids, the amino group may be at other than at the α position, the side chains may be varied, the amino group may be mono-substituted, and the like. For the phosphate esters, particularly oligonucloetides, one may employ hydrogen, amino and sulfur analogs thereof, as well as lower oxidation states, e.g. phosphonamides, phosphorthioates, phosphites, etc., substitution of the phosphate group with other dibasic acids, e.g. carbonate, varying the source of the hydroxyl groups, e.g. varying the monosaccharides, using 5 or 6 membered sugars, substituting the oxygen with nitrogen or sulfur, or the like. Instead of the naturally occurring purines and pyrimidines of nucleosides, other bases may be employed or totally different side groups may be employed to enhance the variety of the oligomer. The side groups may be selected with varying conformations, charges, functional groups, or the like, so long as the side groups do not interfere with the oligomerization, nor the presence of the galactosyl epitope.

In the case of the oligomeric combinatorial libraries, the galactosyl epitope may be introduced in a variety of ways. Depending upon the nature of the chemistry, the galactosyl group may be introduced in association with one or more of the monomeric groups. Alternatively, the galactosyl epitope may be provided as the last unit, employing any convenient functionality for adding to the final functionality of the oligomer. As is well known in the preparation of oligomeric compounds, various groups are protected, so that they are unreactive during the course of the synthesis. These groups may be deprotected at the end of the reaction series. See, for example, U.S. Pat. Nos. 4,833,902; 5,182,366; 5,010,175; and 5,270,170; and WO93/06121; WO94/06291; WO92/10588; and WO92/09300, as exemplary. For the most part, the oligomers are prepared by extension of the chain while bound to a solid surface, which may be a particle, silicon chip, or other convenient solid support. The linkage which is involved will normally be either chemically or photolytically cleavable, so as to release the desired compound from the support. A wide variety of techniques have been developed for synthesizing oligomers and providing for identification of the particular oligomer. See, for example, WO92/00091; WO94/02515; WO93/20242; WO94/06017; WO94/04558;. WO91/17823; and Cho et al., Science (1993) 261:1303.

Where the library is a non-oligomeric library, the synthetic strategy will incorporate the ability to introduce the galactosyl epitope at a convenient stage of the synthesis. For the most part, this will be the last stage, where all of the members of the library may be brought together in the same vessel or aliquoted into different vessels, for introduction of the galactosyl epitope.

Various chemistries may be employed for joining the galactosyl epitope to a variety of functionalities. See, for example, Gobbo et al., *Int. J. Pept. Protein Res.* (1992) 40:54–61; Wood and Wetzel, *Bioconjug. Chem.* (1992) 3:391–6; Filira et al., *Int. J. Pept. Protein Res.* (1990) 36:86–96; Kazimierczuk et al., *Z. Naturforsch.* (1985) 40:715–720; Rademann and Schmidt, *Carbohydr. Res.* (1995) 269:217–25; and Wong et al., *Glycoconj. J.* (1993) 10:227–234. The particular manner in which the galactosyl epitope is joined to the oligomeric monomer, oligomer, or synthetic organic compound of the library is not critical to this invention, so long as the galactosyl epitope is available for binding to antibodies in the blood.

The number of galactosyl moieties will be at least one, and with the synthetic compounds usually not more than two, while with the oligomers, the number may be up to the number of oligomers, usually not more than one-half the number of oligomers, more usually, not more that one-fifth the number of oligomers, conveniently not more than a total of five, more conveniently, not more than a total of three.

For screening the compounds, the assay will provide for a detectable signal associated with the binding of the compound to a protein or cellular target. Depending on the nature of the assay, the detectable signal may be light absorbance or emission, plaque formation, or other convenient signal. The result may be qualitative or quantitative.

For screening the compounds for specific binding, various immunoassays may be employed for detecting human (or primate) antibodies bound to the cells. Thus, one may use labeled anti-hIg, e.g. anti-hIgM, hIgG or combinations thereof to detect specifically bound human antibody of the galactosyl epitope. Various labels can be used such as radioisotopes, enzymes, fluorescers, chemiluminescers, particles, etc. There are numerous commercially available kits providing labeled anti-hIg, which may be employed in accordance with the manufacturer's protocol.

For screening the compounds for cytotoxic effects, a wide variety of protocols may be employed to ensure that one has the desired activity. One will normally use cells, which may be naturally occurring or modified, cell lines, or the like. The cells may be prokaryotic or eukaryotic. For example, if one is interested in a pathogen, where it does not matter to which epitope the compound-galactosyl conjugate binds, one can combine the pathogenic cells with each of the compounds in the presence of an antibody dependent cytotoxic system to determine the cytotoxic effect. One may perform this assay either prior to or subsequent to determining the effect of the various candidate compounds on cells of the host to whom the compound would be administered. In this way, one would obtain a differential analysis between the affinity for the pathogenic target and the affinity for host cells which might be encountered, based on the mode of administration.

In some situations, one would be interested in a particular cellular status, such as an activated state, as may be present with T cells in autoimmune diseases, transplantation, and the like. In this situation one could first screen the compounds to determine those which bind to the quiescent cell, and as to those compounds which are not binding to the quiescent cells, screen the remaining candidate compounds for cytotoxicity to the activated cells. One may then screen for other cells present in the host which might be encountered by the compounds to determine their cytotoxic effect. Alternatively, one might employ cancer cells and normal cells to determine whether any of the compounds have higher affinity for the cancer cells, as compared to the normal cells. Again, one could screen the library of compounds for binding to normal cells and determine the effect. Those compounds which are not cytotoxic to normal cells could then be screened for their cytotoxic effect to cancer cells. Even where some cytotoxicity exists for normal cells, in the case of cancer cells, where there is a sufficient differentiation in cytotoxic activity, one might be willing to tolerate the lower cytotoxicity for normal cells, where the compound is otherwise shown to be effective with cancer cells.

Instead of using cells which are obtained naturally, one may use cells which have been modified by recombinant techniques. Thus, one may employ cells which can be grown in culture, which can be modified by upregulating or downregulating a particular gene. In this way, one would have cells which differ as to a single protein on the surface. One could then differentially assay the library as to the effect of members of the library on cells for which the particular protein is present or absent. In this way, one could determine whether the compound has specific affinity for a particular surface membrane protein as distinct from any of the proteins present on the surface membrane.

One may differentiate between cells by using antibodies binding to a particular surface membrane protein, where the antibodies do not initiate the complement dependent cytotoxic effect, for example, using different species, isotypes, or combinations thereof. By adding the antibodies, blocking antisera or monoclonal antibodies, to one portion of the cells, those cells will not have the target protein available for binding to the library member. In this way one creates comparative cells which differ in their response based on the unavailability in one group of a single protein. While antibodies will usually be the most convenient reagent to use, other specific binding entities may be employed which provide the same function.

For use in the assay to determine binding, one may use an antibody dependent cytotoxic system. For the most part, it is convenient to use human whole blood or plasma which contains the antigalactosyl antibody and complement for cytotoxic effect. However, one could use synthetic mixtures of the ingredients, where only those components necessary for the cytotoxic effect are present. This may be desirable where components of blood or plasma may adversely affect the results of the assay.

Also, while a cellular lawn is an extremely convenient way to screen large numbers of candidates, other techniques may also find use. These techniques include the use of multiwell plates, and the various devices used for the preparation of the combinatorial library, such as pins, tea bags, etc. One may grow the cells separately in relation to the nature of the various devices, where the device may then be contacted with the cells or have the cells grown on the device. The device may be immersed in an appropriate culture, seeded with the cells, or otherwise provided for contact between the cells and the candidate compound. After adding the cytotoxic agent, one may then analyze for lysis in a variety of ways. FACS may be used for distinguishing between live and dead cells, $^{51}$Cr release may be employed, or detection of an intracellular compound in the supernatant, may serve to detect active compounds.

In addition, one may wish to know whether the compound has agonist or antagonist activity. The subject assay techniques provide for a rapid way for determining those compounds present in the library which bind to the target protein. Once, one has substantially narrowed the number of candidate compounds, one can use more sophisticated assays for detecting the activity of the compound itself. In this way, one can perform a rapid screen to determine binding affinity and specificity, followed by a more intensive screen to determine activity. Various techniques exist for determining activity, where the cells may be modified, so that a marker gene will be activated which will provide for a detectable signal. Conveniently, the signal may be associated with production of a dye, the production of a surface membrane protein which can be detected with labeled antibodies, or the secretion of a protein which can be detected in the supernatant by any of a variety of techniques. For example, the gene which is expressed may be luciferase modified to have a leader sequence so as to be secreted, whereby the supernatant can then be screened for light generation formation by using an appropriate substrate.

Various protocols may be employed for screening the library. To some degree this will depend upon the nature of the preparation of the compounds. For example, the compounds may be bound to individual particles, pins, membranes, or the like, where each of the compounds is segregatable. In addition, the amount of compound available will vary, depending upon the method employed for creating the library. Furthermore, depending upon the nature of the attachment of the compound to the support, one may be able to release aliquots of a compound, so as to carry out a series of assays. In addition, the manner in which the compounds are assayed will be affected by the ability to identify the compound which is shown to have activity.

Where the compounds are individually on a surface in a grid, so that at each site of the grid one knows what the composition is, one can provide a cellular lawn which is similarly organized as a grid and may be placed in registry with the compounds bound to the solid surface. Once the lawn and solid substrate are in registry, one may release the compounds from the surface in accordance with the manner in which the compounds are attached. After sufficient time for the compounds to bind to the proteins on the cellular surface, one may wash the cellular lawn to remove non-specifically bound compounds. One or more washings may be involved, where the washings may provide for varying degrees of stringency, depending upon the desired degree of affinity. After the washings have been completed, mammalian blood or plasma may then be added and incubated for sufficient time for cytotoxicity. The plasma or blood may then be removed and plaques observed, where the nature of the compound may be determined by virtue of the position in the grid. Of course, the plasma or blood should be free of any components which would naturally kill the cells of the lawn.

Since the preparative process may be repeated, one could prepare a plurality of solid substrates, where the same compounds are prepared at the comparable sites, so that the screening could be repeated with the same or different cells to determine the activity of the individual compounds.

In some instances, the identity of the compound can be determined by a nucleic acid tag, using the polymerase chain reaction for amplification of the tag. See, for example, WO93/20242. In this instance, the compounds which are active may be determined by taking the lysate and introducing the lysate into a polymerase chain reaction medium comprising primers specific for the nucleic acid tag. Upon expansion, one can sequence the nucleic acid tag or determine it's sequence by other means, which will indicate the synthetic procedure used to prepare the compound.

Alternatively, one may have tagged particles where the tags are releasable from the particle and provide a binary code which describes the synthetic procedure for the compounds bound to the particle. See, for example, Ohlmeyer, et al., PNAS U.S.A. (1993) 90:10922. These tags can conveniently be a homologous series of alkylene compounds, which can be detected bar gas chromatography-electron capture. Depending upon the nature of the linking group, one may provide for partial release from the particles, so that the particles may be used 2 or 3 times before identifying the particular compound.

While for the most part libraries have been discussed, any large group of compounds can be screened analogously, so long as the galactosyl epitope can be joined to each of the compounds. Thus, compounds from different sources, both natural and synthetic, including macrolides, oligopeptides, ribonucleic acids, dendrimers, etc., may also be screened in an analogous manner.

Formation of a plaque in the assay demonstrates that binding of the member of the library to the cell, usually a surface protein, does not interfere with the α-galactosyl epitope binding to an antibody, that the immune complex is sufficiently stable to initiate the complement cascade, and that the member has a high affinity for the target.

The subject methodology finds particular application in any situation where one has a cellular target to be killed, particularly those cellular targets having low or no α-gal epitope. Thus, the cellular target may be a prokaryote, which is pathogenic. Various organisms include Microbacterium, Yersinia, Pseudomonas, *Bordetella pertussis, Treponema pallidum, Neisseria gonorrhoea,* Streptococcus, *Hemophilus influenza,* etc. Other pathogens include eukaryotes, particularly fungi, such as Candida, Histoplasma, etc., and protozoa, e.g. Giardia. In addition, viruses which provide for surface membrane proteins in infected cells, can also be the target of the subject compounds, where the cells that are screened have been virally infected.

Host cells may also serve as targets, where the cells are either abnormal or act in an adverse way to the host or treatments of the host. For example, cancerous tissues which can be distinguished from normal tissue can serve as a target for the subject compounds. T or B cells associated with autoimmune diseases or associated with GVHD or transplant rejection may also serve as targets. Aberrant cells, regardless of their nature, so long as they can be distinguished from normal cells, may also serve as targets. Thus, psoriatic lesions, lymphoma cells, bacterial, fungal, parasitic, virus infected cells, may be targets of the subject products. Also, where one wishes to ablate a portion of cells, without removal of all of the cells, such as cells expressing a differiation marker such as T cell subsets, activated platelets, endothelial cells, hormone or cytokine receptor expressing cells, the subject compounds may find application.

The subject compounds may be modified to act as vehicles for the transport of various agents to a specific target. The α-galactosyl group may be replaced with a number of different groups, such as chelating agents, particularly for chelating radiolabels, toxins, detectable labels, antibiotics, cytotoxic agents, haptens, e.g. ABO, HBsAg, etc. Alternatively, the subject compounds, with or without the α-galactosyl group, may be radiolabeled for in vivo diagnosis or treatment.

The subject compounds may be administered in a wide variety of ways, depending upon the nature of the compound, the nature of the indication, the frequency of administration, the need for acute verses chronic treatment, and the like. The subject compounds may be formulated in accordance with common physiologically acceptable formulations, as liquids or powders, and the like. Various carriers may be employed, such as water, phosphate buffered saline, mineral oil, vegetable oil, alcohols, fatty acid esters, alum, sugar, etc. The dosage of the active compound will vary widely, depending upon the particular purpose as described above, and can readily be determined empirically in accordance with known ways. The subject compounds may be administered as powders, liquids, aerosols, capsules, from depots, tablets, and the like. The subject compositions may be administered parenterally, orally, or by inhalation. Administration may be intravascular, peritoneally, intramuscularly, subcutaneously, transdermally, intralesionally, and the like.

The subject compounds may be used in assays, where one is interested in which one of many alternatives are present. This can be particularly applicable where one is interested in the presence of one or a few alleles, such as in the major histocompatibility complex, blood typing, pathogenic strains, etc. By screening cells with the various alleles, one can identify compounds which specifically bind to each of the alleles. One can then prepare a multicompound device comprising a library of compounds, where each site has a different compound specific for a particular target compound. By contacting the library of compounds with the cells and detecting lysis, one can rapidly determine which of the various target compounds are present.

The following examples are offered by way of illustration and not by way of limitation.

EXPERIMENTAL

Identification of a therapeutic specific for human CD4 by preparation and screening of a polypeptide combinatorial library containing an αGal moiety.

The synthesis of the library first requires the generation of an αGal disaccharide with a reactive group on the first carbon of the galactosyl ring. Briefly this is accomplished by generating two bromine protected ring compounds (2,3,4,6-tetra-O-benzyl-α-D-galactopyranosyl bromide and 4,6-O-benzylidene-1,2-O-isopylidene-α-D-galactopyranose). The two structures are joined in a sterically controlled synthesis to yield 2,4,6,2',3',4',6'-hepta-O-acetyl-3-O-α-D-galactopyranosyl-α-D-galactopyranosyl bromide. Treatment of the latter compound with methanolic solution of sodium methoxide replaces the bromide with a thioglycoside of 3-thiopropionic acid. This terminal group is reactive with free amines resulting in a covalent bond resistant to known proteases and glycosidase digestion. In order to complete the synthesis of a reagent permitting the incorporation of the αGal residue into a combinatorial library, this structure is added to the secondary amine of arginine (termed αGal-s-R where R is arginine in the single letter amino acid code).

Combinatorial chemistry works best when ligands are constructed around a known core binding sequence. The core sequence is used as a starting point for the derivatization of high affinity-high specificity ligands. Furthermore, identification of the core sequence is most straightforward when it is derived from a known biological interaction. Hence, the following peptide epitope scan was performed to identify such core sequences from the 307–332aa stretch of the gp120 molecule from the human immunodeficiency virus-1 known to be important in its interaction with human CD4. Overlapping 14mer peptides covering the entire length of the gp120 binding region are generated using f-moc chemistry. These peptides incorporate the αGal-s-R epitope at the amino terminal of the 14mer sequence.

The limited library of overlapping peptides generated in this way is assayed for binding to soluble CD4. This is performed as follows: Soluble CD4 (Intracell: Boston, Mass.) is spotted on a nitrocellulose membrane in a 96 well dot blot apparatus at 10 μg/ml in carbonate coating buffer pH 9.6. The membrane is washed in phosphate buffered saline (PBS) and saturated with 5% bovine serum albumin (BSA; N.B. BSA is not glycosylated, therefore it has no terminal αGal residues that could interfere with the assay). Each peptide containing the αGal tag is added to an individual well at 1 μg/ml and incubated at 37° C. for two hours. The membrane is again washed and then incubated with BSIB4 lectin (Sigma Chemical Co., St. Louis, Mo.) coupled to horse radish peroxidase (HRP: N.B. BSIB4 is a lectin specific for terminal αGal sugars). After another two hours of incubation at 37° C. and another round of washing, the presence of bound lectin conjugate is demonstrated by incubation with o-phenylaminediamine (OPDA: Sigma). The reaction is stopped by the addition of 2.5N HCl, and results evaluated by the eye.

This analysis yields two core motifs for the construction of the true combinatorial library 1) RIQR and 2) FVTI. The first motif is selected for further derivatization because of its enhanced binding characteristics, and the fact that the presence of two charged arginines will lead to the development of a soluble hydrophilic compound. A first 13mer combinatorial hybritope library is generated containing the core sequence and a terminal sugar residue: αGal-s-R-XXX-B1-RIQR-B2-XXX where B1 and B2 could be any of the L or D amino acids and are defined whereas X is not yet determined. The combinatorial peptides are linked to αGal-2-R through the arginine free primary amine. This yields 1,600 known permutations of a 13mer containing a single αGal carbohydrate.

This library is synthesized and tested in a complement dependent manner. A human CD4+ clone (SUP-T1: ATCC, Rockville, Md.) is labeled by incubation at 37° C. for two hours in excess $^{51}Cr$ (Amersham, Arlington Hts., Ill.). The cells are washed and aliquoted at 10,000 cells per well in 17 microtiter plates. All subsequent steps are performed on ice to prevent immunomodulation of the peptide/antibody bound CD4. Each compound is added to a different well at a concentration of 1 μg/ml. Human anti-αGal antibodies immunaffinity purified from a melibiose column (Sigma: melibiose contains terminal αGal residues) are added to each well at a final concentration of 2.3 μg/ml. Complement (Class I: One lambda, Canoga Park, Calif.) is added to the wells at a final dilution of 1:10 and incubated for one hour. The plates are centrifuged for five minutes and the supernatants harvested. After drying, the amount of $^{51}Cr$ released into the medium following complement mediated lysis of the cells bound to peptide and antibody is assessed in a gamma counter.

The greatest amount of $^{51}Cr$ release indicates the strongest binding of the αGal bearing hexamer. The B1 and B2 combinations giving the best results are chosen and used for the definition of an additional two residues. In this manner the iterative process is continued until a defined 13mer containing a single αGal residue has been isolated.

The specificity and utility of this combinatorial product are then tested. The αGal-13mer is assayed for lysis of CD4 cells among normal human peripheral blood lymphocytes. This is done by removing the white cells from the red over a Ficoll density gradient. Simple fluorescence activated cell sorting (FACS) using anti-CD4 antibodies demonstrates the presence of this T cell subpopulation. The cells are then incubated with αGal-13mer, the natural human anti-αGal antibodies and complement, where this population is eliminated. A second FACS analysis of the sample demonstrates the disappearance of the CD4+ cells.

Furthermore, the ability of the product to function in the serum of many individuals is tested. SUP-T1 cells are labeled and incubated with αGal-13mer and then with a number of fresh human serum samples. The natural human anti-αGal antibodies and the native complement lyses the labeled targets. The supernatants are harvested and analyzed in a gamma counter.

It is evident that the subject methods and compositions find broad application, particularly where one wishes to develop a compound for cytotoxic activity. Any of the commonly available combinatorial techniques may be employed for producing large libraries, where each of the compounds in the library has the galactosyl epitope. In this way, one may define compounds which have high specificity and affinity for a particular target of a cell and are capable of initiating the complement cascade, so as to induce ablation of the cells in vivo.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

what is claimed is:

1. A method for detecting specific binding of a member of a library of compounds to a protein on the surface of a cell, wherein the members of said library of compounds are characterized by comprising a galactosyl epitope, said method comprising:

(a) contacting a first group of cells with members of said library, wherein:
   (i) said first group of cells comprise said protein on the surface thereof,
   (ii) the interaction between the cells of said first group and each of said members of said library is individually distinguishable; and
   (iii) said contacting is performed under conditions which allow binding of one or more of said members of said library to said first group of cells;
(b) contacting a second group of cells with the same members of said library, wherein said second group of cells do not comprise said protein on the surface thereof;
(c) separating non-specifically bound members from said first and second groups of cells;
(d) contacting said first and second groups of cells with a cytotoxic composition comprising anti-galactosyl antibodies or an antibody dependent cytotoxic system reactive with the gal epitope; and
(e) determining lysis of said first and second group of cells, wherein the lysis of cells of said first group and the absence of lysis of cells of said second group indicates the specific binding of said member to said protein.

2. A method according to claim 1, wherein said cells are prokaryotic.

3. A method according to claim 1, wherein said cells are eukaryotic.

4. A method according to claim 1, wherein said cytotoxic composition comprises blood or plasma containing anti-galactosyl antibodies.

5. A method according to claim 1, wherein said first and second group of cells are contacted as cellular lawns.

6. A method according to claim 1, wherein one of said first and second groups of cells consists of normal cells and the other of said first and second groups of said cells consists of an aberrant form of said normal cells.

7. A method according to claim 1, wherein said members of said library are oligomers.

8. A method according to claim 7, wherein said oligomers are oligopeptides.

9. A method according to claim 7, wherein said oligomers are oligonucleotides.

* * * * *